United States Patent [19]
Iyer et al.

[11] Patent Number: 5,640,470
[45] Date of Patent: Jun. 17, 1997

US005640470A

[54] FIBER-OPTIC DETECTORS WITH TERPOLYMERIC ANALYTE-PERMEABLE MATRIX COATING

[75] Inventors: Lokanathan M. Iyer, Redmond, Wash.; Yanqun Zhao, Gurnee, Ill.

[73] Assignee: Abbott Laboratories, Abbott Park, Ill.

[21] Appl. No.: 410,810

[22] Filed: Mar. 27, 1995

[51] Int. Cl.$^6$ .............................. G02B 6/00; G01N 21/64
[52] U.S. Cl. ..................... 385/12; 422/82.06; 422/82.07; 128/634
[58] Field of Search ..................... 385/12, 116, 129, 385/130; 422/82.06, 82.07; 128/634

[56] References Cited

U.S. PATENT DOCUMENTS

| | | | |
|---|---|---|---|
| 4,434,249 | 2/1984 | Ballestrasse et al. | 521/27 |
| 4,925,268 | 5/1990 | Iyer et al. | 385/12 |
| 5,000,901 | 3/1991 | Iyer et al. | 385/12 X |
| 5,047,627 | 9/1991 | Yim et al. | 250/227.23 |
| 5,049,383 | 9/1991 | Huth et al. | 424/405 |
| 5,098,659 | 3/1992 | Yim et al. | 422/82.07 |
| 5,119,463 | 6/1992 | Vurek et al. | 385/129 |
| 5,120,510 | 6/1992 | Gourley et al. | 422/82.07 |
| 5,127,077 | 6/1992 | Iyer et al. | 385/116 |
| 5,378,432 | 1/1995 | Bankert et al. | 422/82.07 |

FOREIGN PATENT DOCUMENTS

| | | |
|---|---|---|
| 0 286 008 | 12/1988 | European Pat. Off. |
| 37 08 451 | 6/1988 | Germany |
| 62-270135 | 11/1987 | Japan |
| 62-294950 | 12/1987 | Japan |

OTHER PUBLICATIONS

*Chemical Abstracts*, vol. 108, 1988, p. 292; Japanese Patent No. 62-270,135. No month available.
*Chemical Abstracts*, vol. 109, 1988, p. 117; Japanese Patent No. 62-294,950. No month available.
*Chemical Abstracts*, vol. 110, 1989, p. 111; European Patent No. 286,008. No month available.
*Chemical Abstracts*, vol. 111, 1989, p. 305; German Patent No. DE 3,708,451. No month available.

*Primary Examiner*—Rodney B. Bovernick
*Assistant Examiner*—Hemang Sanghavi
*Attorney, Agent, or Firm*—Christensen O'Connor Johnson & Kindness PLLC

[57] ABSTRACT

The invention provides fiber-optic detectors with rapid response times for measuring analytes in aqueous solutions, including blood. The detectors, because of their size, accuracy, and sterilizability may be used in vitro. In a preferred embodiment, pellets comprising a unique, permeable terpolymer of methyl methacrylate, butyl acrylate and methacrylamidopropyltrimethylammonium chloride; and an indicator for an analyte are used as the detecting element of a fiber-optic sensor. Response times for pH testing are better than 150 seconds at t90%. The pellets are easily made by solvent casting techniques and failure rates are low.

20 Claims, 1 Drawing Sheet

FIBER-OPTIC DETECTORS WITH TERPOLYMERIC ANALYTE-PERMEABLE MATRIX COATING

FIELD OF THE INVENTION

This invention relates to fiber-optic detectors for monitoring pH and blood analyte concentrations. More particularly, the analyte-permeable matrix of the invention comprises a terpolymer that provides enhanced permeability so that time for analyte concentration and pH detection time are significantly reduced.

BACKGROUND OF THE INVENTION

In recent years, fiber-optic chemical sensors have been developed to detect the presence, and monitor the concentration of, various analytes. These analytes include oxygen, carbon dioxide, glucose, inorganic ions, and hydrogen ions, in both liquids and gases. These sensors rely on the recognized phenomenon that the absorbance, and in some cases the luminescence, of certain indicators is specifically perturbed in the presence of certain analytes. The perturbation of the luminescence and/or absorbance profile of the indicator can be detected by monitoring radiation that is absorbed, reflected, or emitted by the indicator when it is illuminated in the presence of a specific analyte. Thus, fiber-optic probes have been developed that position an analyte-sensitive indicator in a light path. These probes may include a pair of optical fibers. One fiber transmits electromagnetic radiation from a light source to the indicator; the other fiber transmits the return light from the indicator to a light sensor for measurement. Typically, the indicator is housed in a sealed chamber with walls permeable to the analyte. Alternatively, the probe may comprise only one optical fiber. An example of a single fiber-optic physiological probe may be found in U.S. Pat. No. 4,925,268, which is hereby fully incorporated by reference.

A fiber-optic pH probe may include an ion-permeable membrane envelope that encloses the distal ends of a pair of optical fibers. The envelope is a short section of dialysis-type tubing that fits closely about the two fibers. A pH-indicating dye-containing solid material (e.g., phenol red/methyl methacrylate copolymer microbeads) is packed tightly within the membrane distal to the ends of the fibers. A cement is applied to seal the distal end of the membrane, and also the proximal end, where the optical fibers enter the membrane. The membrane has pores sized to allow passage of hydrogen ions, but sufficiently small to preclude passage of dye-containing solid material. During operation, the probe optically detects the change in color of the pH-sensitive dye by monitoring the intensity of light reflected or absorbed by the dye at a specific wavelength. One of the fibers is connected at its proximal end to a light source, while the other fiber is connected at its proximal end to a light sensor. Light is backscattered through the dye from one fiber into the other fiber. In preparing the dye-containing material, light-scattering polystyrene microspheres of about 1 micron diameter may be added, prior to incorporation of the dye material into the hollow membrane. Fiber-optic probes for analytes other than pH can be constructed similarly using appropriate indicator compositions that undergo a change in absorbance or luminescence that is detectable by a light sensor.

As previously indicated, fiber-optic chemical sensors can be made using a single optical fiber. Single-fiber sensors reduce production costs and those coated with an indicator-containing matrix reduce calibration problems significantly. Such single-fiber probes are also small enough to pass through a hypodermic needle, and flexible enough to be threaded through blood vessels for physiological studies. The '268 patent discloses a drift-free fiber-optic sensor that has an analyte-permeable matrix disposed in the light path defined by the axial core at one end of a single optical fiber segment. The matrix contains an indicator molecule covalently linked to a preferred copolymer selected from the following: methyl methacrylate/methacrylamidopropyltrimethylammonium chloride, N-vinylpyrrolidone/p-aminostyrene, methyl methacrylate/hydroxymethyl methacrylate, methyl methacrylate/N-vinylpyrrolidone, or methyl methacrylate/acrylic acid. It is further disclosed that these polymers are preferably formulated in the range of from about 60:40 to about 80:20 by wt. %. Further, drift-free performance is obtained with sensors having matrices of these polymers less than 70 microns in thickness.

In order to be commercially useful as a probe or sensor, the device must pass a timed test. Thus, a pH probe, for instance, must reach 90% of the true or equilibrium pH value at a predetermined time, t90%, or fail and be rejected. Whereas the fiber-optic sensors of the '268 patent are represented as solving the problems of calibration and reducing manufacturing cost, the '268 patent does not address the issue of response time and that copolymeric matrices are found to have a relatively high, and unpredictable, failure rate that varies from one batch of matrices to the next. Thus, it is desirable to develop fiber-optic sensors and probes that have reduced failure rates; less variation from one matrix batch to another matrix batch; and reduced t90% response times.

SUMMARY OF THE INVENTION

The invention provides fiber-optic physiological probes and sensors for monitoring blood analyte concentrations that have a rapid response time while maintaining accuracy of detection and analysis. The detecting element portion of the fiber-optic probes and sensors of the invention has a unique analyte-permeable matrix that comprises a terpolymer of methyl methacrylate (MMA), butyl acrylate (BA), and methacrylamidopropyltdmethylammonium chloride (MAPTAC). Further, the terpolymer has a permeability to hydrogen ions that allows detection of pH at t90% in less than about 120 seconds, preferably less than about 100 seconds.

The terpolymeric analyte-permeable matrix used in the fiber-optic probes and sensors of the invention permit free passage of an analyte substance through the matrix. Further, the matrix is hydrophilic for ease of application in aqueous solutions or mixtures, such as blood. However, the hydrophilicity of the matrix is well controlled, and free of undue swelling, thereby reducing the risk of matrix disassociation from the optical fiber, when immersed in an aqueous solution. Further, the terpolymer used in the invention's fiber-optic sensors and probes is optically clear and optically well matched to the optical fiber core so that light-scattering effects, such as Fresnel losses are minimized.

For ease of application to optical fiber, the terpolymer that forms the analyte-permeable matrix of the fiber-optic sensors of the invention is readily soluble in conventional solvents, especially solvents having high vapor pressures, such as ethanol, 2-ethoxy ethanol, N,N-dimethylacetamide (DMAC), 2-methoxyethanol and the like. Further, a solution incorporating the terpolymer has good film-forming properties for ease of coating onto fiber-optic compositions of glass or organic polymer, such as polymethylmethacrylate; or for ease of making into pellets, often with reflective metal inserts, for attaching adhesively to fiber ends. Moreover, upon drying, the matrix, whether in pellet form or otherwise, is stable and does not shrink or crack. Upon immersion in aqueous solutions, the matrix retains rigidity and strength and has sufficient mechanical strength to be manipulated through blood vessels.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
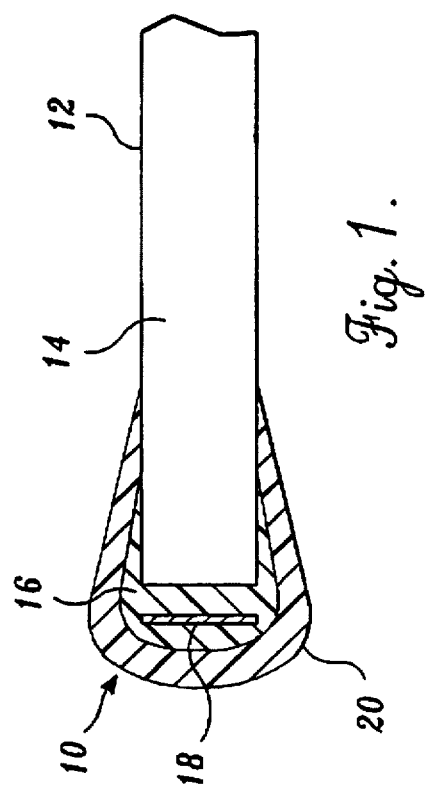
FIG. 1 is a schematic, in cross section, of a fiber-optic sensor according to the invention.

In the specification and claims, the term "fiber-optic detector" means and encompasses both fiber-optic sensors and fiber-optic probes. The term "fiber-optic sensor" means a fiber-optic detector for analyte detection that has a single fiber-optic filament. The term "fiber-optic probe" means a fiber-optic detector for analyte detection that has at least two fiber-optic filaments. The term "analyte" means that which it is desired to detect and analyze in a liquid medium, such as blood. In the case of pH, the analyte is understood to include elements, ions (including hydrogen ions) and chemical compositions that may be tested in order to ascertain pH, such as carbon dioxide, ammonia, and like bases or acids. The term "detecting element" refers to the element at the end of a fiber-optic detector that must be immersed in the liquid to be analyzed and that reacts to the presence or concentration of the analyte. The detecting element generally includes, at a minimum, a polymeric matrix (in pelletized or membrane shape) and an indicator for the analyte (chemically bonded to the matrix or as particulates enclosed in a membranous matrix). Optionally, it may also include other components, such as a metallic reflector, to assist or improve detection.

The invention provides fiber-optic detectors for detecting analytes, especially pH, in a liquid medium, such as blood, plasma, and the like. The sensors and probes are characterized in that a MMA/BA/MAPTAC terpolymer is used as a matrix component of the detecting element of the detector, thereby significantly improving detector response time and also reducing detector reject rates. In certain embodiments of the invention, it is advantageous to mix the MMA/BA/MAPTAC terpolymer with another organic polymeric composition to produce the matrix. The relative proportions of the terpolymer and the other polymeric compositions are selected to retain the desired properties that the terpolymer imparts to the matrix, namely, permeability to analytes, ability to withstand pelletizing with low risk of breakage, and sterilizability with radiation or ethylene oxide.

An indicator for the desired analyte is used in combination with the matrix containing the MMA/BA/MAPTAC terpolymer. Thus, in one embodiment, an indicator molecule is covalently bound to the terpolymer matrix, which is deployed on the distal end of at least one fiber-optic filament to allow detection of changes in matrix light radiation absorbance or luminescence. In another embodiment, the indicator is bound to another polymeric composition, that is commingled with the MMA/BA/MAPTAC terpolymer, to form the matrix attached to the distal end of the fiber-optic filament. In yet another embodiment, the indicator is in the form of particles, such as beads, and is surrounded by and contained in a semipermeable membrane of the terpolymer, which is attached to an end of a fiber-optic filament to form a detecting element.

The unique matrix of the invention comprises a terpolymer that includes MMA, BA, and MAPTAC. In a preferred embodiment, the terpolymer comprises from about 85 to about 60 mole percent MMA, from about 10 to about 25 mole percent BA, and from about 5 to about 10 mole percent MAPTAC. In a more preferred embodiment, the terpolymer comprises from about 80 to about 75 mole percent MMA, from about 13 to about 18 mole percent BA, and from about 6 to about 8 mole per-cent MAPTAC.

The terpolymer useful in the invention has a significantly lower glass transition temperature (about 80°–100° C.) than the copolymer of MMA/MAPTAC disclosed in the '268 patent (which is about 180° C.). As a consequence, the terpolymer is softer and not as subject to brittle fracture. Further, it is theorized without being bound, that the lower glass transition temperature also influences the rate at which hydrogen ions, and other analytes, are able to migrate into a matrix of the terpolymer, thereby significantly improving the response time of the fiber-optic sensors and probes of the invention.

According to the invention, mixtures of the MMA/BA/MAPTAC terpolymer with other polymeric compositions may also be used to produce matrices useful in fiber-optic detectors. Preferably, the mixtures are selected to ensure that a sufficient proportion of the MMA/BA/MAPTAC terpolymer is present so that desired properties are retained. The embodiments using mixtures of the terpolymer with other polymers are especially important when the indicator cannot be bonded to the terpolymer and it is desired to make pellets of indicator-bonded polymeric matrices for use in detecting elements. Under these circumstances, the indicator is first bonded to a suitable reactive polymeric composition, one that is miscible and compatible with the MMA/BA/MAPTAC terpolymer, and that does not significantly adversely affect the advantageous properties of the terpolymer in the quantities needed, for example, MMA/MAPTAC. A quantity of the indicator-bonded polymeric composition is then commingled with the terpolymer to produce a mixture suitable for use in a detecting element according to the invention.

Preferably, any polymeric compositions added to the MMA/BA/MAPTAC terpolymer for commingling, should result in a mixture that may be solvent cast by coating onto metal foil and subsequently dried so that pellets of polymeric mixture with adhered metal reflectors are readily produced. This solvent casting and pelletizing method is preferred for producing pellets, even when only MMA/BA/MAPTAC is used to make pellets, according to the invention. Further, the hardened polymeric mixture, in pelletized form, should be readily adhered to the tips of fiber-optic filaments using conventional adhesives, such as polymethylmethacrylate, and even the MMA/BA/MAPTAC terpolymer itself, in solution with a solvent, such as 2-methoxyethanol. Moreover, the selected other polymeric compositions that are commingled with the MMA/BA/MAPTAC terpolymer should not adversely affect the desirable permeability of the terpolymer to such an extent that analyte diffusion into the polymeric mixture is significantly impaired.

In a preferred embodiment, the matrix allows detection of pH at t90% within a period of less than about 150 seconds, especially less than about 120 seconds; and more preferably in less than about 100 seconds. Furthermore, batches of sensors and probes according to the invention, when prepared in accordance with the customary care taken in the industry, achieve a near 100 percent success rate in achieving a response time of less than about 100 seconds when measuring pH at t90%.

A preferred method of manufacturing a sensor according to the invention is to select a fiber-optic filament and dip its tip into a clear undercoat solution including 2 wt. % PMMA (polymethylmethacrylate) in toluene. The undercoated tip of the optical fiber is then dipped into a pellet attachment solution that includes an about 7.5 wt. % concentration of MMA/BA/MAPTAC terpolymer and MMA/MAPTAC/ phenol red copolymer with a solvent, such as 2-methoxyethanol, to produce a coated tip. Thereafter, a pellet, fabricated as described above, is attached to the still wet coated tip of the optical fiber. When the attachment solution dries, so that the pellet is firmly bonded in place, the tip of the optical fiber, with pellet attached, is dipped into an overcoat solution that typically has the same polymeric components as the attachment solution, except that their combined concentration is about 13 wt. %, although higher concentration solutions may also be used as long as, upon drying, a protective, permeable overcoating forms over the detecting element at the tip of the fiber-optic filament.

Detectors of the invention may be fabricated according to well-known techniques in the industry, with the proviso that the matrix must be made of the MMA/BA/MAPTAC terpolymer, or mixtures of organic polymers that contain the terpolymer. Thus, in an embodiment wherein the indicator is bonded to the terpolymer matrix, a sample of the terpolymer is combined with an indicator composition and allowed to undergo reaction to chemically bond indicator molecules to the terpolymer. If the desired ratio of indicator to terpolymer is exceeded in the reacted mixture, then the indicator-bonded terpolymer is combined with indicator-free terpolymer in such proportion as to produce a mixture with the desired percentage of indicator relative to the combined mass of indicator and terpolymer. For example, in the case of phenol red, the preferred amount of indicator to terpolymer is in the range of about 1 to about 5 wt. % in the detecting element.

This polymer indicator mixture can be applied directly as a coating to the end of the fiber-optic filament to form the matrix or, preferably, pelletized prior to application to the filament. When the mixture is pelletized, then these pellets are adhered, using adhesives known in the art, such as polymethylmethacrylate (PMMA) to an end of the fiber-optic filaments. The ends of these fiber-optic filaments, in combination with the indicator matrices, form a detecting element. Optionally, and preferably, the pellet has a metal reflector. Such pellets are prepared by a solvent-casting process that forms a film of polymer and solvent of desired thickness on a thin metal foil, allowing the solvent to vaporize, then punching a pellet from the foil.

In other embodiments, the terpolymer according to the invention is fabricated into a thin membrane, ranging in thickness from about 30 to about 70 microns. Indicator compositions, in the form of particulates, beads, and the like, are enclosed in this membrane, which is then adhesively attached to an end of a fiber-optic filament. Thus, a fiber-optic sensor or probe according to this embodiment of the invention includes at least one fiber-optic filament with a membrane containing an indicator composition at one end of the fiber-optic filament to form a detecting element for immersion in the liquid containing the analyte to be detected and analyzed. Analyte molecules migrate through the terpolymeric membrane, react with the indicator composition, and produce a transformation in the indicator composition that is detectable by a change in light radiation emission or absorption. Due to the enhanced permeability of the terpolymeric membrane of the invention, relative to the copolymers of the prior art, the response time for detecting and analyzing the analytes is enhanced. Thus, the fiber-optic probes of the invention may be used to detect pH by detecting carbon dioxide, ammonia, and like bases or acids that are able to permeate through the terpolymer. Useful indicators include, for example, phenol red, cresol red, α-cresol, chlorophenol red, carboxynaphtholthaleine, methylene blue, and the like.

In one embodiment of the invention sensors shown in FIG. 1, there is provided a fiber-optic sensor 10 that includes a single fiber-optic filament 12 having bonded to its distal tip 14 a pellet of MMA/BA/MAPTAC terpolymer 16, which includes a chemically bonded indicator. Further, the pellet may include a metallic reflector 18 dispersed therein and in the path of incident light for improving the reflectance of the incident light thereby enhancing the sensitivity of the sensor. A protective permeable coating 20 is preferably disposed over the distal tip of the sensor enclosing the pellet and the reflector.

Figure 2:
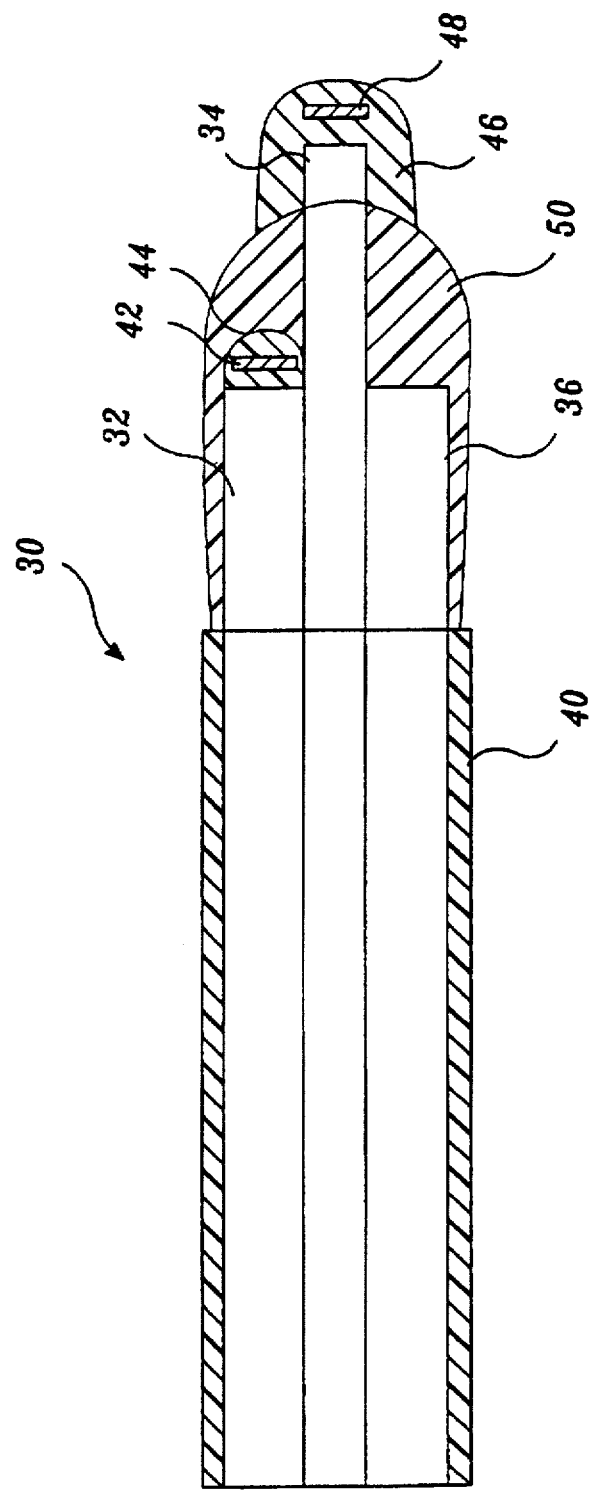
FIG. 2 is a schematic cross-sectional view of a fiber-optic probe with three fiber-optic filaments, according to the invention.

In an exemplary embodiment of a probe according to the invention, shown in FIG. 2, a carbon dioxide sensor 32, a pH sensor 34, and an oxygen sensor 36 are each formed with individual fiber-optic filaments that are bundled together and covered with a sheath 40 so that the distal ends carrying the detecting elements protrude from the sheath. In this particular construct, the distal tip of the carbon dioxide sensor 32 has adhered thereto a pelletized matrix 44 with a metallic reflector insert 42. The pelletized matrix 44 is, according to the invention, made of a mixture of the MMA/BA/MAPTAC terpolymer and an MMA/MAPTAC copolymer, to which is bonded phenol red, as an indicator.

The pH sensor 34 has bonded to its distal tip a matrix 46 containing the MMA/BA/MAPTAC terpolymer in pelletized form, with a metallic reflector 48 contained therein.

The oxygen sensor 36 is made by dipping the distal end of the probe 30 into a silicone elastomeric mixture containing an oxygen-sensitive indicator, such as platinum tetrafluorophenylporphoryn (PtTFPP). Upon removal from the dipping mixture, the mixture forms a hardened bead 50 at the tip of the probe, which initially covers the distal ends of each of the carbon dioxide, oxygen, and pH sensors. This bead is permeable to carbon dioxide, so that the carbon dioxide sensor is not affected by the silicone bead coating that covers its tip, including the matrix 44 and metallic reflector 42. However, the silicone material is not hydrophilic, and would affect the performance of the pH sensor 34. Therefore, a solvent is used to remove any coating of the silicone material that may have formed over the detecting element at the distal tip of the pH sensor 34. The cleaned, silicone-free distal tip of the pH sensor is then dipped into a polymeric mixture that, upon hardening, is permeable to hydrogen ions in aqueous solution to allow pH detection. This coating over the tip of the pH sensor is preferably a composition that includes the MMA/BA/ MAPTAC terpolymer, either alone or in combination with other polymeric compositions, according to the invention.

In a preferred embodiment, the fiber-optic sensor or probe filaments are fabricated from organic polymers, which provide more bonding sites for adhesion of the terpolymer matrix to the filament. Further, the polymeric filaments have advantages over glass filaments, including bendability, thinness, low cost, and ease of cleaving to form single-filament fiber-optic sensor detecting elements.

In a preferred embodiment, the terpolymeric analyte-permeable matrix includes a covalently bonded indicator molecule, which is selected to respond optically in the presence of the targeted analyte substance when it is immobilized in the indicator matrix. Preferably, for continuous monitoring of analyte concentration, the reaction or response between the indicator molecule and the analyte is reversible, as well as sensitive and specific. The indicators that bond to the terpolymer include, for example, platinum tetrafluorophenylporphoryn and phenol red, among others.

The following examples illustrate only certain aspects of the invention and do not limit the scope-of the invention, as described above and claimed herebelow.

EXAMPLES

EXAMPLE 1

Response times for pH sensors made according to the invention.

In each of the Examples, the pellets of the detecting elements of the sensors were made from a solvent cast mixture of 15 wt. % MMA/MAPTAC copolymer with phenol red grafted thereto, and 85 wt. % MMA/BA/MAPTAC terpolymer. The steps for preparation of MMA/MAPTAC and the grafting of phenol red to the copolymer are set forth in U.S. Pat. No. 4,925,268 (which is incorporated by reference), specifically Examples 1, 2, and 3.

In order produce a terpolymer containing 80 mol % MMA, 13 mol % BA, and 7 mol % MAPTAC, the following components were reacted at 70° C., and under nitrogen at about atmospheric pressure: 4.3 ml MMA, 0.9 ml BA, 1.45 ml 50% aqueous solution of MAPTAC, 5 ml ethanol, and 50 mg. of an initiator azobisisobutyronitrile (AIBN). The terpolymer produced was mixed with MMA/MAPTAC copolymer with phenol red grafted in an 85:15 weight proportion and the mixture was solvent cast from a 2-methoxyethanol solution and the resultant film was punched to make pellets for use with a fiber-optic sensor for testing pH. A total of eight sensors were produced. Each was affixed to the tip of an optical fiber by coating the fiber tip with a 5 wt. % solution of PMMA in toluene; attaching the pellet to the tip of the fiber using the same solution used to cast the pellet; and overcoating the fiber tip (with adhered pellet) with the solution used to cast the pellets. The resultant fiber-optic sensors were used to test the pH of an isotonic phosphate buffer through which carbon dioxide had been bubbled. Readings were compared against a control reading provided by a Corning 178 blood gas analyzer (produced by Ciba-Corning).

The results showed an average response time at t90% of 1.31±0.08 minutes.

A second set of 15 sensors were similarly prepared and sterilized with ethylene oxide. Thereafter, the sensors were used to test pH and provided an average response time at t90% of 1.54±0.24 minutes. Only two sensors failed to meet a response time requirement of 2.00 minutes.

Another batch of the terpolymer was prepared, intending the same 80/13/7 mol % composition as before, except that the components used were as follows: 4.25 ml of MMA, 0.9 ml of BA, 1.45 ml of 50% aqueous solution of MAPTAC, 5 ml of ethanol, and 30 mg. of AIBN. Once again, the terpolymer and copolymer/indicator mixture was solvent cast and pelletized. A total of 29 sensors were produced and subjected to sterilization using ethylene oxide. After sterilization, the sensors exhibited an average response time at t90% of 1.37±0.22 minutes. All of the sensors tested met the requirement of having a response time of less than two minutes.

A third terpolymer of composition 79.3 mol % MMA, 12 mol % BA, and 8 mol % MAPTAC, was prepared using the following components: 2.00 ml of a 50% aqueous solution of MAPTAC, 4.55 ml MMA, 1.75 ml BA, 40 mg. AIBN, and 6 ml ethanol. Using this material and an MMA/MAPTAC copolymer grafted with phenol red, as before, pellets were prepared from a solvent cast film and 25 pH sensors were produced. Some of these sensors were sterilized with ethylene oxide, others were not. Results indicated a t90% response time of 1.5±0.2 minutes, with insignificant variation between sterilized and nonsterilized sensors.

While the preferred embodiments of the invention have been described, one of skill in the art will appreciate that various changes can be made without departing from the spirit and scope of the invention as described above and claimed herebelow.

We claim:

1. A fiber-optic blood analyte detector comprising:
   at least one fiber-optic filament with an end having a detecting element for immersion in blood to be analyzed, the detecting element comprising an analyte-permeable matrix for detecting analytes in said blood, the matrix comprising:
   (i) a terpolymer of methyl methacrylate, butyl acrylate and methacrylamidopropyltrimethylammonium chloride; and
   (ii) an indicator for analytes to be detected in blood;
   wherein said matrix has a permeability to the analytes that allows detection of pH at t90% in less than about 150 seconds.

2. The detector of claim 1, wherein the matrix is a terpolymer comprising from about 85 to about 60 mole percent methyl methacrylate; from about 10 to about 25 mole percent of butyl acrylate; and from about 5 to about 10 mole percent of methacrylamidopropyltrimethylammonium chloride.

3. The detector of claim 1, wherein the matrix is in a pelletized form and is adhesively bonded to the end of at the least one fiber-optic filament; and the indicator is chemically bonded to the matrix.

4. The detector of claim 3, wherein the indicator is selected from the group consisting of phenol red, methylene blue, cresol red, chlorophenol red, carboxynaphtholthaleine, and α-chlorocresol.

5. The detector of claim 3, wherein the detecting element further comprises a metallic reflector.

6. The detector of claim 5, further comprising a protective semipermeable membrane over the matrix.

7. The detector of claim 1, wherein the matrix is in the form of a membrane adhesively attached to at least the end of the at least one filament.

8. The detector of claim 7, wherein the indicator is in the form of particles, said particles enclosed by the membrane so that light emitting from one end of a fiber-optic filament impinges on said particles, is reflected from said particles, and is then detected.

9. The detector of claim 8, wherein the indicator is selected from the group consisting of cresol red, chlorophenol red, carboxynaphtholthaleine, and α-chlorocresol.

10. A fiber-optic blood analyte detector comprising:
    at least one fiber-optic filament with an end having a detecting element for immersion in blood to be analyzed; the detecting element comprising an analyte-permeable matrix for detecting analytes in said blood, the matrix comprising a terpolymer comprising from about 85 to about 60 mole percent methyl methacrylate, from about 10 to about 25 mole percent butyl acrylate, and from about 5 to about 10 mole percent of methacrylamidopropyltrimethylammonium chloride; and an indicator for analytes to be detected in blood.

11. The detector of claim 10, wherein the matrix has a thickness ranging from about 15 to 50 microns.

12. The detector of claim 10, wherein the matrix comprises an indicator selected from the group consisting of phenol red, methylene blue, cresol red, chlorophenol red, carboxynaphtholthaleine, and α-chlorocresol chemically bonded to the terpolymer.

13. The detector of claim 12, wherein the detecting element further comprises a metallic reflector.

14. The detector of claim 13, further comprising a protective semipermeable membrane over the matrix.

15. The detector of claim 10, wherein the matrix is in a pellet form and is adhesively bonded to the end of at the least one fiber-optic filament.

16. The detector of claim 15, wherein the detecting element further comprises a metallic reflector; and the matrix is covered with a protective semipermeable coating.

17. The detector of claim 10, wherein the matrix is a thin membrane enclosing a particulate indicator, said membrane adhesively bonded to the end of the at least one fiber-optic filament.

18. A fiber-optic detector for detecting changes in the pH of blood, comprising:

at least one fiber-optic filament with a detecting element at one end thereof for immersion in blood to be analyzed for pH; the detecting element comprising:

(i) an analyte-permeable matrix comprising a terpolymer of from about 85 to about 60 mole percent methyl methacrylate, from about 10 to about 25 mole percent butyl acrylate, and from about 5 to about 10 mole percent methacrylamidopropyltrimethylammonium chloride; and (ii) an indicator sensitive to and changing light reflected therefrom in response to changes in hydrogen ion concentration, wherein said matrix has a permeability to hydrogen ions that allows detection of pH at t90% in less than about 150 seconds.

19. The detector of claim 18, wherein the matrix is in the form of a pellet adhered to the one end of at the least one fiber-optic filament, and the indicator is chemically bonded to the terpolymer of the matrix.

20. The detector of claim 18, wherein the matrix is in the form of a membrane surrounding the indicator, in particulate form, the membrane adhesively attached to the one end of the at least one fiber-optic filament.

* * * * *

UNITED STATES PATENT AND TRADEMARK OFFICE
CERTIFICATE OF CORRECTION

PATENT NO. : 5,640,470
DATED : June 17, 1997
INVENTOR(S) : L.M. Iyer et al.

It is certified that error appears in the above-indentified patent and that said Letters Patent is hereby corrected as shown below:

| COLUMN | LINE | |
|---|---|---|
| 9 | 7 | "methacrylarnidopropyltrimethylammonium" should read --methacrylamidopropyltrimethylammonium-- |

Signed and Sealed this

Seventh Day of October, 1997

Attest:

BRUCE LEHMAN

*Attesting Officer*     *Commissioner of Patents and Trademarks*